US005629175A

United States Patent [19]

Goodman et al.

[11] Patent Number: 5,629,175

[45] Date of Patent: *May 13, 1997

[54] MOLECULAR FARMING

[75] Inventors: Robert M. Goodman; Vic C. Knauf, both of Davis; Catherine M. Houck, Vacaville; Luca Comai, Davis, all of Calif.

[73] Assignee: Calgene, Inc., Davis, Calif.

[*] Notice: The term of this patent shall not extend beyond the expiration date of Pat. No. 4,956,282.

[21] Appl. No.: 463,182

[22] Filed: Jun. 5, 1995

Related U.S. Application Data

[63] Continuation of Ser. No. 164,346, Dec. 8, 1993, Pat. No. 5,550,038, which is a continuation of Ser. No. 507,380, Apr. 9, 1990, abandoned, which is a continuation of Ser. No. 760,236, Jul. 29, 1985, Pat. No. 4,956,282.

[51] Int. Cl.$^6$ ............... C12N 15/12; C12N 15/20; C12N 15/82; C12N 5/04
[52] U.S. Cl. ............... 435/69.1; 435/69.4; 435/69.51; 435/70.1; 435/172.3; 536/23.5; 536/23.52; 800/205; 800/DIG. 43
[58] Field of Search .................. 435/69.1, 70.1, 435/69.4, 69.51, 172.3, 240.4; 800/205, 250, 255, DIG. 17, DIG. 43; 536/23.5, 23.52

[56] References Cited

U.S. PATENT DOCUMENTS

| | | | |
|---|---|---|---|
| 4,399,216 | 8/1983 | Axel et al. | 435/6 |
| 4,530,901 | 7/1985 | Weissman | 435/70 |
| 4,956,282 | 9/1990 | Goodman et al. | 435/69.51 |
| 5,550,038 | 8/1996 | Goodman et al. | 435/70.1 |

FOREIGN PATENT DOCUMENTS

| | | |
|---|---|---|
| 0073646 | 8/1982 | European Pat. Off. . |
| 0095350 | 11/1983 | European Pat. Off. . |
| 0108580 | 5/1984 | European Pat. Off. . |
| 0135291 | 3/1985 | European Pat. Off. . |
| WO83/02425 | 9/1981 | WIPO . |
| WO84/02920 | 8/1984 | WIPO . |
| WO84/00466 | 8/1984 | WIPO . |
| WO84/02913 | 8/1984 | WIPO . |
| WO84/02919 | 8/1984 | WIPO . |
| WO85/04899 | 11/1985 | WIPO . |
| WO87/00551 | 1/1987 | WIPO . |
| WO91/02066 | 2/1991 | WIPO . |

OTHER PUBLICATIONS

Lefebvre, et al., "Mammalian Metallothione in Functions in Plants", *Biotechnology*, Canada, (1987), vol. 5:1053–1056.

Sijmons, et al., "Production of Correctly Processed Human Serum Albumin in Transgenic Plants", *Biotechnology*, The Netherlands, (1990), vol. 8:217–221.

Hiatt, et al., "Production of Antibodies in Transgenic Plants", *Biotechnology*, La Jolla, California (1989) vol. 342:77–78.

Odell, et al., "Identification of DNA Sequences Required for Activity of *The Cauliflower Mosaic Virus 35S Promoter*" New York (1985), vol. 313:810–812.

Herrera–Estrella, et al., "Agrobacterium as a Vector System for the Introduction of Genes into Plants", *Plant Genetic Engineering*, Cambridge Press, University, (1985), New York, pp. 61–93.

Fraley, et al., *Biotechnology* (1985) 3:629–635.

Odell, et al., *Nature* (1985) 313:810–812.

Velten, et al., *EMBO* (1984) 3:2723–2730.

Leemans, et al., *Molecular Biology of Plant Tumors* (1982) Academic Press, New York pp. 537–545.

Jaynes and Strobel, *International review of Cytology* (1981) Supp 13:105–125.

Depicker et al., Genetic Engineering of Plant Cells–An Agr. Persp. (1983) Plenum Press, New York pp. 4803–4807.

Fraley, et al., *Proc. Natl. Acad. Sci.* USA (1983) 80:4803–4807.

Shaw, et al., *Gene* (1983) 23:315–330.

Tuite M. F., et al., "Regulated high efficiency expression of human interferon–alpha in *Saccharomyces cerevisiae*" (1982) The EMBO Journal 1:603–608.

Rogers, S. C., et al., "Investigation of Factors Involved in Foreign Protein Expression in Transformed Plants". *Biotechnology in Plant Science* (1985) pp. 219–227.

Gray, P. W. et al., *Proc. Natl. Acad. Sci*, USA vol. 80:5842–5846 (1983).

Odell, J. T., et al, "Identification of DNA sequences required for activity of the cauliflower mosaic virus 35S promoter", *Nature*, vol. 313:810–812.

Eichboltz, D., et al., *Somatic Cell and Molecular Genetics* vol. 13:67–76 (1987).

Yip, Y.K., et al. *Proc. Natl. Acad. Sci. USA Biochemistry* vol. 79:1820–1824 (1982).

Stryer L. page 719–720.

*Primary Examiner*—David T. Fox

[57] ABSTRACT

Novel constructs are provided for expression of physiologically active mammalian proteins in plant cells, either in culture or under cultivation. The constructs provide a promoter functional in a plant host, a structural gene coding for mammalian protein and a terminator functional in a plant host. The construct is introduced into a plant cell to become integrated into the plant genome for expression in the plant cells or plants. The plant cells may be harvested and the mammalian protein isolated in physiologically active form.

8 Claims, No Drawings

MOLECULAR FARMING

This is a continuation of application Ser. No. 08/164,346, filed Dec. 8, 1993, now U.S. Pat. No. 5,550,038, which is a continuation of application Ser. No. 07/507,380, filed Apr. 9, 1990, now abandoned, which is a continuation of application Ser. No. 06/760,236, filed Jul. 29, 1985, now U.S. Pat. No. 4,956,282.

BACKGROUND OF THE INVENTION

1. Field of the Invention

An extensive literature has been developed demonstrating the ability to produce polypeptide sequences in a wide variety of cellular hosts. Numerous genes have been isolated from mammals and viruses, joined to transcriptional and translational initiation and termination regulatory signals from a source other than the structural gene and introduced into hosts in which the regulatory signals are functional. Frequently, the peptide of interest is prepared to be used for a physiological purpose. In many situations, physiological activity requires not only having the correct or substantially correct amino acid sequence, but the peptide must fold properly including proper disulfide linkage formation and may require further processing, such as acetylation, glycosylation or methylation.

For economic production, one would wish to use unicellular microorganisms, which could be grown in large fermentation tanks, do not have fastidious nutrient requirements and are relatively economical to maintain. Bacteria, such as *E. coli*, *B. subtilis*, or the like, fungi, such as yeast, Candida, filamentous fungi, or the like, offer economic opportunities to produce a wide variety of peptides. However, because of the substantial difference in the nature of the unicellular microorganisms and mammalian cells, the folding and processing in a mammalian cell appears to be substantially different from these lower order organisms. Therefore, the products which are obtained from the unicellular microorganisms may not have been properly processed or folded so as to realize a substantial proportion or all of the physiological activity of the naturally occurring peptide obtained from a native host.

There therefore remains substantial interest in providing alternative economic systems for producing peptides, where high yields may be obtained and significantly, the products may be produced in a form providing for a high degree of physiological activity common to the wild-type peptide having the same or substantially the same amino acid sequence.

BRIEF DESCRIPTION OF THE RELEVANT LITERATURE

References concerned with expression of various interferons include Goeddel et al., *Nucleic Acids Res.* (1980) 8:4057–4074; Goeddel, *Nature* (1980) 287:411–415; Yelverton et al., *Nucleic Acids Res.* (1981) 9:731–741; Gray et al., *Nature* (1982) 295:503–508; Devos et al., *Nucleic Acids Res.* (1982) 10:2487–2501; Grey and Goeddel, *Proc. Natl. Acad. Sci. USA* (1983) 80:5842–5846; Scahill et al., *Proc. Natl. Acad. Sci. USA* (1983) 80:4654–4658. See also, Horsch et al., *Science* (1985) 227:1229–1231.

Wide host range cloning vectors are described by Knauf and Nester, *Plasmid* (1982) 8:45–54. The nucleotide sequence of the T-DNA region is described by Barker et al., *Plant Molecular Biology* (1983) 2:335–350. See also, EPA 0 116 718 and PCT WO84/02913.

SUMMARY OF THE INVENTION

Efficient production of physiologically active mammalian proteins is provided by introducing functional constructs containing the mammalian structural gene into a plant cell. The construct is able to express the desired peptide in an isolatable form. The plant cells may be grown in culture or cultivated in an appropriate nutrient medium or soil and the mammalian protein harvested. Particularly, T-DNA transformation may be employed for integration of the construct into the plant genome under conditions where the cells can be used to produce plants.

DESCRIPTION OF THE SPECIFIC EMBODIMENTS

Novel DNA sequences are provided comprising constructs functional in plant cells for the expression of physiologically active mammalian peptides. The constructs provide for functional transcriptional and translational initiation and termination regulatory signals which with the construct integrated into the plant genome, provide for efficient expression of the structural gene. Depending upon whether the cells are grown in culture or cultivated in soil or other medium, these cells or plants may be harvested, and the desired product extracted and purified in accordance with conventional techniques.

The construct for introduction into the plant will be considered first. While the construct may be either DNA or RNA, for the most part, the construct will be DNA even though the construct may be ultimately introduced into the plant cell as RNA, such as a virus. One significant element of the construct will be the transcriptional cassette involving the transcriptional initiation region, which may be divided into a regulatory domain and the usually proximal RNA polymerase binding domain, the structural gene coding for the mammalian peptide of interest, and a terminator region which provides for termination of transcription and translation. Another significant element is the regulation of expression at a particular stage of differentiation, in a particular plant part, e.g., roots, leaves, stalk, or the like. In many situations a polypeptide leader signal will be desirable which directs the product to a particular organelle. This will be of substantial significance where the organelle may be involved in the proper processing of the peptide.

A wide variety of transcriptional initiation regions may be employed, which are inducible, e.g., tissue specific, or constitutive. The transcriptional initiation regions may come from the tumor-inducing plasmids of Agrobacterium, particularly the genes associated with T-DNA, or from viruses, or plants. Among the T-DNA transcription initiation regions which may find use include those regions associated with octopine synthase, nopaline synthase, mannopine synthase, transcript 7, and the like. Among viral transcriptign initiation regions are included the caulimovirus full length promoter and the region VI promoter. Among plant transcription initiation regions are the ribulose-1,5-bisphosphate carboxylase small subunit region, which is light inducible, or the napin or other seed protein region, for formation in seed.

The transcription initiation regions may be isolated from their natural sites in a host or may be sequenced and synthesized so as to have the same or substantially the same sequence as the wild-type region. Where inducible regulation is desired, domains may be obtained from different sources, so that a regulatory domain may be obtained from one source and joined to an RNA polymerase binding domain from a different source. In this manner, one may provide for the use of strong RNA polymerase binding domain associated with one structural gene, while having a regulatory domain associated with a different structural gene. These hybrid regulatory regions may find particular use where one wishes to induce the production of the desired gene at a particular phase in the growth of the plant or to have the product located in a particular plant part, such as seed, leaves, or the like. Any transcriptional termination regulatory region may be used which is functional in plants, e.g., prokaryotic or eukaryotic, from T-DNA, plants, viruses or mammals.

The structural gene may be any mammalian gene of interest, which includes mammalian viral pathogen genes. A wide variety of genes have been isolated and shown to be capable of production in unicellular microorganisms, to various degrees of biological activity and efficiencies, and in mammalian cells, with the ever present concern that the mammalian cells are transformed cells, so that any product must be carefully purified to ensure the complete absence of any nucleic acid contaminant. Structural genes of interest include $\alpha$-, $\beta$- and $\gamma$-interferons, immunoglobulins, with the structural genes coding for the light and heavy chains and desirably assembly occurring in the plant cell, lymphokines, such as interleukins 1, 2 and 3, growth factors, including insulin-like growth factor, epidermal growth factor, platelet derived growth factor, transforming growth factor-$\alpha$, -$\beta$, etc., growth hormone, insulin, collagen plasminogen activator, blood factors, such as factors I to XII, histocompatibility antigens, enzymes, or other mammalian proteins, particularly human proteins.

Among the antigens associated with viral pathogens, include the core and envelope proteins of leukemia and lymphotropic retroviruses, such as HTLV-I, -II and -III, feline leukemia virus, etc., surface antigens of herpes simplex virus, hepatitis B virus, adenovirus, and the like.

Peptides of interest other than those indicated above will be peptides which may be administered physiologically, where growth in plants diminishes the probability of contaminants causing an adverse response upon administration to a mammalian host.

Plants may also find use in preparing other proteins than to be administered to a host, where the mammalian protein, such as an enzyme, may require folding and/or processing that is unavailable in unicellular microorganisms. Not only may plants be used to prepare the mature peptide, but in many instances it may be desirable to prepare the precursor, which may require cleavage and assembly, either endogenous or exogenous to the plant. Peptides can be prepared having a naturally occurring transit or leader peptide or a transit or leader peptide from a plant peptide. The transit peptide will serve to subject the entire peptide product to the processing and maturing of the peptide. Such processing may include specific peptide cleavage, e.g., removal of the transit peptide, glycosylation at glycosylation sites, folding with appropriate formation of disulfide linkages.

Any convenient terminator may be employed which provides for efficient termination in conjunction with a particular transcriptional initiation region. The terminator may be the terminator region normally associated with the transcriptional initiation region or associated with a different transcriptional initiation region, so long as the region is functional in plants.

In order to select for plant cells that have successfully integrated the construct, the expression construct or cassette will usually be joined to a marker. The marker will allow for either screening or selection, usually selection. A number of different antibiotic resistance genes are known that can find use in plants to serve as markers. These genes include enzymes providing resistance to kanamycin, chloramphenicol, G418, gentamycin, and the like. These genes will have transcriptional and translational initiation and termination regulatory regions that may be the same or different from the regions employed for the structural gene of interest. Usually constitutive expression will be provided, rather than inducible expression.

In addition to the cassette and marker, depending upon the manner in which the DNA construct will be introduced into the plant cell, other sequences may be necessary. Where the Agrobacterium tumor-inducing system is to be employed, one or both of the T-DNA boundaries of a Ti- or Ri-plasmid will be present, particularly the right boundary region. Each boundary region will generally be of about 1 to 1.5 kbp.

The DNA construct of the cassette, marker and T-DNA may then be employed in a variety of ways. For integration into a Ti- or Ri-plasmid, the construct may be introduced into an appropriate Agrobacterium strain carrying the tumor-inducing plasmid, whereby the construct will become integrated into the tumor-inducing plasmid and may then be transferred to plant cells. Alternatively, the construct may be joined to a broad spectrum replication system, such as a P1 incompatibility replication system and transformed into an Agrobacterium containing an armed or disarmed tumor-inducing plasmid. Integration will occur and transfer to the plant cell of the construct along with other genes and markers. When transfer is with an armed tumor-inducing plasmid (Ti or Ri T-DNA containing plasmid) genes conferring tumor formation will be transferred, so that galls may form. With disarmed tumor plasmids (lacking T-DNA) the tumor-causing genes cannot be transferred and gall formation is not encountered. A transposon may be employed containing the construct and the gene coding for transposase, such as in the Ac-Ds system. A viral system may be employed which provides for integration into the host genome.

Transfer of the DNA construct into the plant cell may be by infection with *A. tumefaciens* or *A. rhizogenes,* microinjection, liposome fusion, viral infection, or the like. The particular manner in which the DNA is introduced into the plant cell for integration is not critical to this invention.

Usually, the construct will be joined to a prokaryotic replication system, for example, a system functional in *E. coli,* so as to allow for cloning at the various stages of preparation of the construct. A wide variety of replication systems are available, both plasmid and phage, such as ColE1, $\lambda$, etc.

Plant cells which are employed may be either monocots or dicots and will be chosen in accordance with the manner in which the desired gene is to be produced and harvested. Plants which may find use include tobacco, sunflower, corn, sugar cane, soybean, tomato, alfalfa, mustard, sugar beet, rapeseed, etc. The product may be found in plant parts such as seed, leaves, fruit, roots, stalks, tubers, or combinations thereof. Thus, the peptide of interest may be the sole purpose for growing the plant or be an additional product.

The construct will be prepared in conventional ways. DNA sequences may be detected by employing probes, which may be designed based on known amino acid sequences or prior isolation of all or fragments of mRNA or chromosomal DNA. The sequences may be restriction mapped or sequenced and the entire gene obtained by various techniques, such as walking, using a plurality of primers, or the like. Once the sequence has been isolated, it may be ligated to other sequences, either directly or through linkers, where the linkers may provide no or portions of coding sequences. Various strategies may be devised based on available restriction sites, the absence of restriction sites, the ability to introduce restriction sites, the availability of particular fragments, the presence of sequences which require excision, and the like. The particular strategy will be dependent upon the gene which is employed, the particular regulatory systems, the availability of vectors having one or more of the desired sequences, as well as other practical considerations.

The manner in which the construct is introduced into plants may be varied widely. This has already been indicated by virtue of the different sequences which may be included in the construct. Of particular interest is the presence of T-DNA for integration in conjunction with the vir genes of the Ti-plasmid which may be present on a plasmid other than the plasmid containing the foreign gene. Thus, the necessary genetic capability for integration into the plant cell can be provided, in conjunction with infection with Agrobacterium or introduction of the DNA by other means. Descriptions of introduction of DNA into plants may be found in Pedersen et al., *Plant Cell Reports* (1983) 2:201–204; Hooykaas-Van Slogteren et al., *Nature* (1984) 311:763–764; de Cleene and de Ley, *The Botanical Review* (1976) 42:389–466, and references cited therein, are incorporated herein by reference.

The transformed plant cells will then be grown in appropriate nutrient medium to provide for selected calli, where plant cells or protoplasts have been modified. Once the calli has formed, the medium may then be changed to encourage root and shoot formation and the resulting shoots transferred to appropriate growth medium for growth of plants. When the plants have been grown to the desired stage, the plants or plant parts, e.g., seeds, fruit or the like, may be harvested, and the desired product isolated in accordance with conventional ways. Thereafter, the gene may be regenerated from seeds, so that the process of regeneration from calli need not be repeated. The plant may be ground and extracted with appropriate solvents, chromatographed, crystallized, solvent extracted, etc. The crude product may then be purified in accordance with the nature of the product.

In some instances it may be neither necessary nor desirable to extract and isolate the mammalian protein product from the plant. Where the product can have a physiological effect on ingestion, it may be sufficient that the product be retained with the plant. This will be true where the plant part is edible, such as fodder which could include nutritional qualities, such as bovine growth hormone, seed, nuts, fruit, and vegetables, which could include proteins involved in the regulation of digestion, or the like.

The following examples are offered by way of illustration and not by way of limitation.

EXPERIMENTAL

The HindIII-SmaI fragment of Tn5 containing the entire structural gene for APHII (Jorgensen et al., *Mol. Gen.* (1979) 177:65) was cloned into pUC8 (Vieira and Messing, *Gene* (1982) 19:259), converting the fragment into a HindIII-EcoRI fragment, since there is an EcoRI site immediately adjacent to the SmaI site. The PstI-EcoRI fragment containing the 3'-portion of the APHII gene was then combined with an EcoRI-BamHI-SalI-PstI linker into the EcoRI site of pUC7 (pCGN546W). Since this construct does not confer kanamycin resistance, kanamycin resistance was obtained by inserting the BglII-PstI fragment of the APHII gene into the BamHI-PstI site (pCGN546X). This procedure reassembles the APHII gene, so that EcoRI sites flank the gene. An ATG codon was upstream from and out of reading frame with the ATG initiation codon of APHII. The undesired ATG was avoided by inserting a Sau3A-PstI fragment from the 5'-end of APHII, which fragment lacks the superfluous ATG, into the BamHI-PstI site of pCGN546W to provide plasmid pCGN550.

The EcoRI fragment containing the APHII gene was then cloned into the unique EcoRI site of pCGN451, which contains an octopine synthase cassette for expression, to provide pCGN552.

pCGN451 includes an octopine cassette which contains about 1556bp of the 5' non-coding region fused via an EcoRI linker to the 3' non-coding region of the octopine synthase gene of pTiA6. The pTi coordinates are 11,207 to 12,823 for the 3' region and 13,643 to 15,208 for the 5' region as defined by Barker et al., *Plant Mol. Biol.* (1983) 2:325.

The 5' fragment was obtained as follows. A small, subcloned fragment containing the 5' end of the coding region, as a BamHI-EcoRI fragment was cloned in pBR322 as plasmid pCGN407. The BamHI-EcoRI fragment has an XmnI site in the coding region, while pBR322 has two XmnI sites. pCGN407 was digested with XmnI, resected with Bal31 nuclease and EcoRI linkers added to the fragments. After EcoRI and BamHI digestion, the fragments were size fractionated, the fractions cloned and sequenced. In one case, the entire coding region and 10 bp of the 5' non-translated sequences had been removed leaving the 5' non-transcribed region, the mRNA cap site and 16bp of the 5' non-translated region (to a BamHI site) intact. This small fragment was obtained by size fractionation on a 7% acrylamide gel and fragments approximately 130 bp long eluted. This size fractionated DNA was ligated into M13mp9 and several clones sequenced and the sequence compared to the known sequence of the octopine synthase gene. The M13 construct was designated p14, which plasmid was digested with BamHI and EcoRI to provide the small fragment which was ligated to a XhoI to BamHI fragment containing upstream 5' sequences from pTiA6 (Garfinkel and Nester, *J. Bacteriol.* (1980) 144:732) and to an EcoRI to XhoI fragment containing the 3' sequences. The resulting XhoI fragment was cloned into the XhoI site of a pUC8 derivative, designated pCGN426. This plasmid differs from pUC8 by having the sole EcoRI site filled in with DNA polymerase I, and having lost the PstI and HindIII site by nuclease contamination of HincII restriction endonuclease, when a XhoI linker was inserted into the unique HincII site of pUC8. The resulting plasmid pCGN451 has a single EcoRI site for the insertion of protein coding sequences between the 5' non-coding region (which contains 1,550 bp of 5' non-transcribed sequence including the right border of the T-DNA, the mRNA cap site and 16 bp of 5' non-translated sequence) and the 3' region (which contains 267 bp of the coding region, the stop codon, 196 bp of 3' non-translated DNA, the polyA site and 1,153 bp of 3' non-transcribed sequence). pCGN451 also provides the right T-DNA border.

The resulting plasmid pCGN451 having the ocs 5' and the ocs 3' in the proper orientation was digested with EcoRI and the EcoRI fragment from pCGN551 containing the intact kanamycin resistance gene inserted into the EcoRI site to provide pCGN 552 having the kanamycin resistance gene in the proper orientation.

This ocs/KAN gene was used to provide a selectable marker for the trans type binary vector pCGN587.

The 5' portion of the engineered octopine synthase promoter cassette consists of TiA6 DNA from the XhoI at bp 15208–13644 (Barker's numbering), which also contains the T-DNA boundary sequence (border) implicated in T-DNA transfer. In the plasmid pCGN587 the ocs/KAN gene from pCGN552 provides a selectable marker as well the right border. The left boundary region was recloned from the HindIII-EcoRI fragment as a KpnI-EcoRI fragment in pCGN565 to provide pCGN580. pCGN565 is a cloning vector based on pUCS-Cm, but containing pUC18 linkers. pCGN580 was linearized with BamHI and used to replace the smaller BglII fragment of pVCK102 (Knauf and Nester, Plasmid (1982) 8:45), creating pCGN585. By replacing the smaller SalI fragment of pCGN585 with the XhoI fragment from pCGN552 containing the ocs/KAN gene, pCGN587 was obtained.

pCGN807 is derived from pBR322, contains the tetracycline resistance gene, has about 300 bp of a sequence including the trp promoter 5' to a 750 bp sequence including all of the murine γ-interferon structural cDNA and a 3'-untranslated region, with the gene described in Gray and Goeddel, Proc. Natl. Acad. Sci. USA (1983) 80:5842–5846. The promoter and gene are an EcoRI fragment of about 834 bp. pCGN807 was digested with EcoRI and HpaI which fragment was inserted into pEMBL18+, which had been digested with EcoRI and SmaI creating pCGN808. pEMBL18+ (Dente et al., Nucleic Acids Res. (1983) 11:1645) differs from the pEMBL plasmids in having the pUC18 linker inserted into the β-galactosidase gene. pCGN808 was digested with EcoRI and BamHI to provide a 540 bp fragment which was inserted into pCGN46 which had been digested with EcoRI and BamHI to provide for the murine γ-interferon cDNA gene to be in the proper orientation in relation to the mannopine synthase (mas) 5' transcription initiation region and the ocs 3' transcription termination region (pCGN809).

An approximately 5.5 kbp EcoRI fragment (Eco13 or EcoC) carrying a portion of the T-R DNA (Barker et al., Plant Mol. Biol. (1983) 2:325) including the mannopine synthase promoter region ($P_{MAS}$) was cloned in a vector designated pVK232. After digestion of pVK232 with EcoRI, Eco13 was inserted into the EcoRI site of pACYC184 to yield plasmid pCGN14. pCGN14 was digested with SphI and ClaI (respectively at position 21562 and 20128 of the Barker et al. sequence, Supra) to remove the $P_{MAS}$ region which was inserted into pUC19 (Pharmacia, Inc.) which had been digested with SphI and AccI to yield pCGN40. The $P_{MAS}$ region includes a ClaI recognition site internally which is methylated, so as to resist digestion.

pCGN40 was digested with EcoRV and EcoRI where the EcoRV site is in the T-DNA, while the EcoRI site is in the polylinker of pUC19 to provide a fragment having the $P_{MAS}$ region. pCGN451 containing the octopine synthase cassette was digested with SmaI and EcoRI and the larger fragment isolated from which the octopine synthase 5' region had been removed. The EcoRV-EcoRI $P_{MAS}$ region was substituted into pCGN451 for the octopine synthase 5' region, where the transcriptional initiation and termination regions were separated by a polylinker to provide pCGN46.

To introduce the plasmid pCGN809 onto the wide host range T-DNA binary vector pCGN587, pCGN809 was transformed into an E. coli polA1 mutant containing pCGN587. The two plasmids pCGN587 and pCGN809 share two regions of homology where recombination can occur: at the ocs 3' regions of the APHII gene and the γ-interferon gene, and at the pUC origins of the two plasmids, recombination at either site results in a plasmid containing both the γ-interferon gene and the APHII gene as intact expression units. In the polA1 mutant, the pCGN809 plasmid, which has a pUC origin of replication, can only survive by integration into the pCGN587 plasmid, which has a wide host range replication system. Since the pCGN809 construct has ampicillin resistance, the chimeric plasmid pCGN810 can be selected. The transformed E. coli host was grown in a nutrient medium containing 100 µg/ml ampicillin and surviving clones isolated. Plasmid pCGN810 was then mated into A. tumefaciens C58 (Watson et al., J. Bacteriol. (1974) 123:255) by the method of Ditta et al., Proc. Natl. Acad. Sci. USA (1978) 77:7347. pCGN810 was also mated into A. tumefaciens K61, which contains a disarmed Ti-plasmid, as compared to C58 which has the genetic capability for nopaline expression, and is an armed Ti-plasmid. The transformed Agrobacterium was selected with carbenicillin (50 µg/ml) and streptomycin (150 µg/ml) at 30° C. for two to three successive streak outs. After growth under selection, DNA was isolated and restricted with BamHI and EcoRI and verified by probe hybridization. The cloned pCGN808 was used as the nick-translated probe and confirmed the presence of a 565 bp γ-interferon fragment in both the expression vector pCGN46 and the T-DNA plasmid pCGN587 in armed and disarmed Agrobacterium.

Four pCGN810 constructs in both C58 and K61 were cocultivated with Nicotiana tabacum xanthii protoplasts and clumps of transformed cells which were selected in 100 µg/ml kanamycin were transferred to solid media containing kanamycin (100 µg/ml) for further growth and regeneration into plants.

Tobacco leaf disks were cocultivated with pCGN810 in C58 and K61 Agrobacterium strains and the disks transferred to selective media with kanamycin (100 µg/ml) for growth to callus.

Sterile tobacco plants were stem-stab inoculated with A. tumefaciens C58 (pCGN810) resulting in the production of gall tissue which was excised and transferred onto solid media containing kanamycin (100 µg/ml). After considerable callus proliferation, most of the gall-induced callus material was harvested for mRNA and protein analysis. A small portion of the gall-callus material started to shoot on the kanamycin medium without hormones. Once transferred to shooting media, the shoot development looked normal for most of the plantlets, though some were teratoma-like. The plantlets were transferred to rooting medium containing kanamycin (100 µg/ml) and most of the morphology normal plantlets rooted.

The rest of the gall-induced callus material was pooled and used for preliminary expression analysis for γ-interferon as compared with control callus (plant cells transformed with A. tumefaciens C58(pCGN587). After extraction of the plant material and immunoprecipitation with antisera against γ-interferon, the extract was electrophoresed on 15% SDS-PAGE, electroblotted to nitrocellulose and blocked with γ-interferon antisera. Radioactively labeled S. aureus protein A was hybridized to the filter, so as to bind to any immune complexes which had formed. In the transformed plant tissue (A. tumefaciens C58 (pCGN810)), a visible band ran at the same size as the positive control γ-interferon samples.

Analysis of the mRNA obtained after an oligo-dT prep of total RNA was performed using nick-translated isolated gene fragments to the Tn5 kanamycin gene (in pCGN587) and the γ-interferon fragment (in pCGN808). The Northern data showed a message in both pCGN587 and pCGN810 mRNA preps which hybridize to the kanamycin fragment. Only the transformed pCGN810 sample, hybridized to the γ-interferon gene probe showing two mRNA species, each terminating in a different sized noncoding 3'-sequence.

Samples were prepared and bioassayed for murine γ-interferon. The samples were prepared as follows: To frozen tobacco tissue from tissue culture (1.6 or 1.0 g) ground in liquid nitrogen was added 5 or 2.5 ml, respectively, extraction buffer (1M NaCl, 25 mg/ml BSA, 10 mM DTT, 10 mM cysteine, 20 mM NaPO$_4$, pH 7.4) and grinding continued until the mixture was liquid. The liquid was then centrifuged twice at 16K rpm for 20 min, transferring the liquid to a fresh tube after the first separation. The sample was then diluted to 5 ml and 0.5 ml control pore glass beads (CPG) (washed and autoclaved) were added and the mixture agitated at 4° C. for 4 hr. The mixture was then loaded onto a silane treated Pasteur pipette column, the column washed with 3 ml 20 mMNaPO$_4$, 1M NaCl and the product eluted with 5 ml 1M NaCl, 30% ethylene glycol. The material eluted from the column was then dialyzed overnight against 20 mM NaPO$_4$, 1M NaCl. Dialysis buffer was changed once at 3 hr. The dialysed sample was concentrated with a Millipore immersible-CX 10,000 ultrafilter to less than about 1 ml and then a series of dilutions with BSA buffer (1M NaCl, 20 mMNaPO$_4$, pH 7.4, 25 mg/ml BSA) performed. Comparison samples were made from transformed and untransformed tobacco, where no γ-interferon gene was introduced, where the tissue was or was not supplemented with γ-interferon. The following table indicates the results.

TABLE

| Tissue[1] | Dilution[2] | γ-IFN activity[3] |
|---|---|---|
| UT A | 0 | 9 |
|  | 1 | 9 |
|  | 2 | 9 |
|  | 3 | 9 |
| UT B | 0 | 741 |
|  | 1 | 188 |
|  | 2 | 15 |
|  | 3 | 9 |
| T A | 0 | 9 |
|  | 1 | 9 |
|  | 2 | 9 |
|  | 3 | 9 |
| T B | 0 | 9191 |
|  | 1 | 9191 |
|  | 2 | 1042 |
|  | 3 | 261 |
| T-γIFN | 0 | 197 |
|  | 1 | 41 |
|  | 2 | 9 |
|  | 3 | 9 |

[1] UT - untransformed tobacco tissue
T - tobacco tissue transformed with foreign DNA
T - γIFN - tobacco tissue transformed with the murine γ-IFN gene
A - no murine γ-IFN added
B - 5 µg γ-IFN added to 5 ml of sample prior to purification treatment
[2] 0 = 0.5; 1 = 10$^{-1}$; 2 = 10$^{-2}$; 3 = 10 − 3
[3] Assay procedure is described in Yip et al., Proc. Natl. Acad. Sci. USA (1982) 79:1820–1824.

The above results demonstrate that one can produce physiologically active mammalian proteins in plant cells. Stable messages are produced by transcription of the mammalian gene integrated into the plant genome, which message can then be translated into the mammalian product, so as to provide physiologically active proteins. The mammalian proteins can be readily isolated free of deleterious contaminants, such as oncogenic DNA, exotoxins, and the like. In addition, the products can be processed to provide for a mature product having the same or substantially the same structure and composition as the naturally-occurring peptide product.

Although the foregoing invention has been described in some detail by way of illustration and example for purposes of clarity of understanding, it will be obvious that certain changes and modifications may be practiced within the scope of the appended claims.

What is claimed is:

1. A method for producing a mammalian peptide which comprises:

growing tobacco plant cells containing an integrated sequence comprising, a first expression cassette having in the direction of transcription (1) a transcriptional and translational initiation region functional in said plant cells, (2) a structural gene coding for said mammalian peptide, and (3) a termination region, whereby said structural gene is expressed to produce said mammalian peptide.

2. In a method for the production of a foreign peptide in a transgenic dicotyledonous plant cell containing an expression cassette, said expression cassette having in the direction of transcription (1) a transcriptional and translational initiation region functional in said plant cell, (2) a structural gene coding for said foreign peptide, and (3) a termination region, the improvement characterized by:

a structural gene coding for a mammalian peptide as said structural gene coding for said foreign peptide in said expression cassette.

3. A method for producing an interferon which comprises:

growing dicotyledonous plant cells containing an integrated sequence comprising, an expression cassette having in the direction of transcription (1) a transcriptional and translational initiation region functional in said plant cells, (2) a structural gene coding for an interferon, and (3) a termination region, whereby said structural gene is expressed to produce said interferon.

4. A method for producing a mammalian peptide which comprises:

growing dicotyledonous plant cells containing an integrated sequence comprising, a first expression cassette having in the direction of transcription (1) a transcriptional and translational initiation region functional in said plant cells, (2) a structural gene coding for said mammalian peptide, and (3) a termination region, and a second expression cassette comprising in the direction of transcription (1) a transcriptional and translational initiation region functional in said plant cells, (2) a marker gene encoding an enzyme which allows for selection of plant cells expressing said gene, and (3) a termination region, whereby said structural gene is expressed to produce said mammalian peptide.

5. The method of claim 4 wherein said enzyme imparts antibiotic resistance.

6. The method of claim 5 wherein said antibiotic is kanamycin.

7. The method of claim 4 wherein said mammalian peptide is an interferon.

8. The method of claim 4 wherein said dicotyledonous plant cells are grown in culture.

* * * * *